Sept. 10, 1963 P. J. HOWARD Plant Pat. 2,281
ROSE PLANT
Filed Aug. 27, 1962
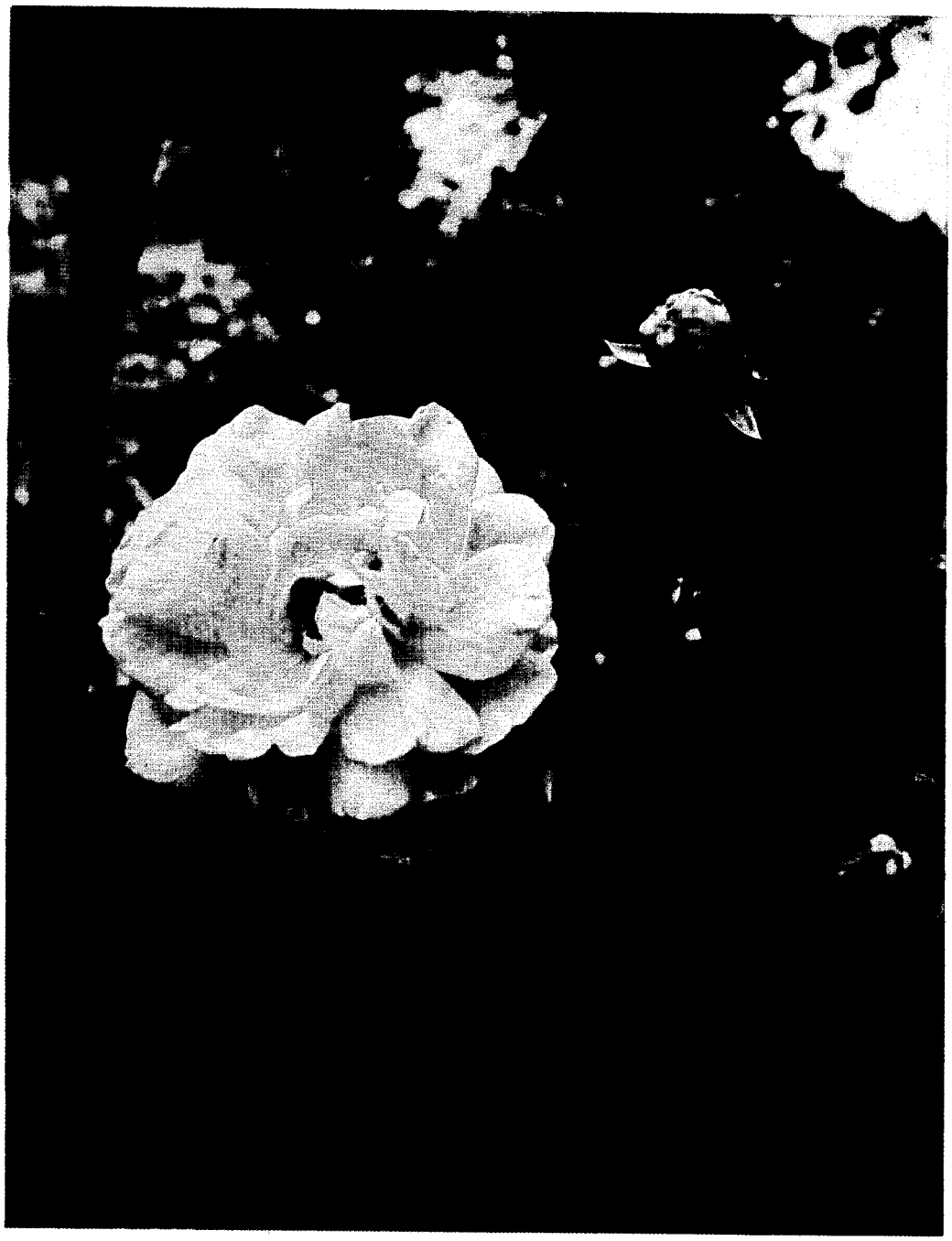
Inventor.
Paul J. Howard
By: Robb & Robb
Attorneys.

United States Patent Office

Plant Pat. 2,281
Patented Sept. 10, 1963

2,281
ROSE PLANT

Paul J. Howard, 11700 National Blvd.,
Los Angeles 64, Calif.

Filed Aug. 27, 1962, Ser. No. 219,805
1 Claim. (Cl. Plt.—19)

The present invention relates to a new and distinct variety of rose plant of the hybrid tea class, which was originated by me by crossing the variety "Peace" (Plant Patent No. 591) with the variety "The Doctor" (unpatented).

The primary objective of this breeding was to produce a new rose variety having the rich flower fragrance of the parent variety "The Doctor," but having better habits of growth. This objective was fully achieved, along with other desirable improvements, as evidenced by the following unique combination of characteristics which are outstanding in the new variety and which distinguish it from its parents, as well as from all other varieties of which I am aware:

(1) Strong, upright, shapely and healthy habits of growth;

(2) A prolific and continuous blooming habit, with the flowers usually borne singly on long, stout stems;

(3) Long, full and pointed-oval flower buds;

(4) Double flower petalage, with the petals having a very good and silky substance;

(5) A distinctive and attractive general color tonality of the flowers corresponding to a glowing deep rose color in the newly opened flowers and changing to bright rose pink in the three-day open flowers;

(6) A strong, rich, spicy flower fragrance; and (7) Good retention of the flower color and fragrance until the petals drop.

My new rose variety more nearly resembles its pollen parent "The Doctor," particularly with regard to its form, as well as its flower fragrance, but it differs from this parent by having a more intense and livelier flower color, with an added silkiness of the flower petals which is probably due in part to an undertone of gold color perceptible only at the very base of each petal. The pointed buds, which can be generally described as oval in shape, are longer than those of the seed parent "Peace," and are more full than those of "The Doctor." The plant is more upright, vigorous and shapely than the plant of either parent variety, and shows no tendency to die back under conditions of severe pruning. As each stem is cut, new growth starts immediately from the remaining growth buds, resulting in continuous production of long-stemmed flowers and increase in the structure of the bush which is taller than average for Hybrid Tea roses, but not as tall as those of the Grandiflora type.

Asexual reproduction of my new variety by budding, as performed by me at Los Angels, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart, except where general color terms of ordinary dictionary significance are obvious:

Type: Half-hardy; tall; bush; outdoor; seedling; for cut flowers and for garden decoration.
Class: Hybrid tea.

Breeding: Seedling.
*Seed parent.*—"Peace."
*Pollen parent.*—"The Doctor."
Propagation: Holds its distinguishing characteristics through succeeding propagations by budding.

*Flower*

Locality where grown and observed: Los Angeles, California.
Flowers borne: Singly; on long, strong stems.
Quantity of bloom: Free, outdoors.
Continuity: Continuous.
Fragrance: Strong. Nature—spicy.
Bud:
*Peduncle.*—Long; medium caliper; erect; almost smooth; with few brown prickles. Color—light reddish green.
*Before calyx breaks.*—Size—large. Form—pointed-oval; with foliaceous appendages on the surface of the bud; with entire foliaceous parts extending beyond the tip of the bud equal to ½ of its length. Color—Emerald Green, 758/ to 758/1.
*As calyx breaks.*—Color—from China Rose, Plate 024 to Currant Red, Plate 821 on outside of petals.
*Sepals.*—Color—green.
*As first petal opens.*—Size—large. Form—pointed-ovoid. Color: outside—from Currant Red, Plate 821/1 to Currant Red, Plate 821/2, inside—Turkey Red, Plate 721.
*Opening.*—Opens up well.
Bloom:
*Size (when fully open).*—Very large; from 4 inches to 5½ inches.
*Petalage.*—Double; from 30 to 45 petals.
*Form.*—Full and high-centered at first, but becoming cupped; petals at first being loosely rolled inward, but later becoming loosely rolled outward at maturity.
Petals:
*Texture.*—Thick; soft. Inside—satiny. Outside—shiny-satiny.
*Shape.*—Outside—obovate, with apex having one notch. Intermediate—obovate, with apex having one notch. Inside—obovate-lanceolate, with apex being rounded, smooth, and sometimes pointed.

This description of a newly opened flower was made from a rose grown outdoors during the month of June at Los Angeles, California:

*Color.*—Outer petal: outside surface—from Turkey Red, Plate 721/1 to Turkey Red, Plate 721/2; inside surface—from Turney Red, Plate 721/2 to Turkey Red, Plate 721/3. Intermediate petal: outside surface—from Carmine, Plate 21 to Carmine, Plate 21/1; inside surface—from Carmine, Plate 21 to Carmine, Plate 21/1. Inner petal: outside surface—from Carmine, Plate 21 to Carmine, Plate 21/1; inside surface—from Carmine, Plate 21, to Carmine, Plate 21/1.

This description was made from a rose that was open for three days outdoors during the month of June at Los Angeles, California:

*Color.*—Outer petal: outside surface—from Rose Madder, Plate 23 to Rose Madder, Plate 23/1; inside surface—from Geranium Lake, Plate 20 to Carmine, Plate 21. Inner petal: outside surface—from Rose Madder, Plate 23 to Rose Madder, Plate 23/1; inside surface—Carmine, Plate 21.
*General color effect.*—Newly opened flower—glowing deep rose. 3-days open—bright rose pink.

*Behavior.*—Drop off cleanly; color is little affected by weather but buds open more rapidly during hot and dry days.

*Flower longevity.*—On bush in garden—4 or 5 days during June. Cut roses grown outdoors and kept at living-room temperatures—3 or 4 days during June.

*Reproductive Organs*

Stamens: Many; regularly arranged about pistils; occasionally few petaloids. Color—Erythrite Red, Plate 0027.

Filaments: Long; most with anthers. Color—reddish.

Anthers: Medium size; open at various times. Color—yellow.

Pollen: Moderate abundance. Color—gold.

Pistils: Many.

Styles: Uneven; short; medium caliper; bunched.

Stigma: Color—red-purple.

Ovaries: Some protruding from calyx.

Hips: Globular. Color—green-russet.

Sepals: Permanent; long; recurved. Color—green. Outside, Paris Green 58/1; reverse, Paris Green 58/3.

Seeds: Few; large.

*Plants*

Foliage:

*Leaves.*—Compound of 5–7 leaflets; abundant; medium large size; heavy; leathery.

*Leaflets.*—Shape—oval, with apex mucronate. Base—obtuse. Margin—simply serrate.

*Color.*—Mature: upper surface—normal green, Spinach Green 960; under surface—normal green, Spinach Green 960/3. Young: upper surface—normal bronze red, Garnet Brown 00918/3; under surface—normal bronze red, Garnet Brown 00918/3.

*Rachis (the supporting stem of the compound leaf).*—Heavy. Upper side—grooved. Under side—moderately thorny.

*Stipules.*—Moderately long; wide; with moderately long points turning out at an angle of less than 45°.

*Disease and insect resistance.*—Average resistance to aphis when insects are present, but better than average resistance to thrips because of tightness of buds as they develop, with consequent little discoloration or malformation of flowers; better than average resistance to mildew when this disease is prevalent, all as determined by comparison with other varieties grown under the same cultural conditions at Los Angeles, California.

Growth:

*Habit.*—Upright; much-branched.

*Growth.*—Free; vigorous.

*Canes.*—Medium caliper.

*Main stems.*—Color—dull green. Thorns—many; medium length; slightly curved downward; with broad base. Prickles—few; color—bronze. Hairs—none.

*Branches.*—Color—bright green. Thorns—many; medium length; with broad base. Prickles—few; color—brown. Hairs—none.

*New shoots.*—Color—bronze red. Thorns—many; long; straight; with broad base. Prickles—few; color—reddish. Hairs—few; color—reddish.

I claim:

A new and distinct variety of rose plant of the hybrid tea class, substantially as herein shown and described, characterized particularly as to novelty by the unique combination of strong, upright, shapely and healthy habits of growth, a prolific and continuous blooming habit, with the flowers usually borne singly on long, stout stems, the production of long, full and pointed-ovoid flower buds, double flower petalage, with very good and silky petal substance, a distinctive and attractive general color tonality of the flowers corresponding to a glowing deep rose color in the newly open flower stage which changes to bright rose pink in the three-day open flowers, a strong, rich and spicy flower fragrance, and good retention of the flower color and fragrance until the petals drop.

No references cited.